United States Patent
Nakayama et al.

[11] 4,233,224
[45] Nov. 11, 1980

[54] CORIOLIN DERIVATIVES

[75] Inventors: Yuya Nakayama, Omiya; Mamoru Kunishima, Tikorozawa; Akira Matsuda, Omiya; Tomio Takeuchi, Tokyo, all of Japan

[73] Assignee: Nippon Kayaku Kabushiki Kaisha, Tokyo, Japan

[21] Appl. No.: 41,904

[22] Filed: May 23, 1979

[30] Foreign Application Priority Data

May 29, 1978 [JP] Japan .................. 53-63321

[51] Int. Cl.³ .................. C07D 493/20; C07D 493/22
[52] U.S. Cl. ................................. 260/343.6
[58] Field of Search ..................... 260/343.6

[56] References Cited

PUBLICATIONS

Umezawa et al., "Coriolin, A New Basidiomycetes Zntibiotic", J. Antibiotics, XXII, 215-217 (1969).
Umezawa et al., "Diketocoriolin B, An Active Derivative of Coriolin B Produced by Coriolus Consors", J. Antibiotics, XXIV, 631-635 (1971).
Umezawa et al., "Revised Structure and Stereochemistry of Coriolins", Tetrahedron Letters, 22, 1955-1958 (1971).
Chemical Abstracts, vol. 79 (1973) 144864p.
E. Ohler et al., Angew. Chem. Internat. Edit., vol. 9 (1970) No. 6, 457-458.
H. O. House, Modern Synthetic Reactions, 2nd ed. (1972) pp. 264-265.
Houben-Weyl, Methoden der Organischen Chemie, vol. VII/2a, Part 1 (1973) pp. 734-737.

*Primary Examiner*—Norma S. Milestone

*Attorney, Agent, or Firm*—Schuyler, Birch, McKie & Beckett

[57] ABSTRACT

Anti-tumor low-toxicity coriolin derivatives represented by the following general formula:

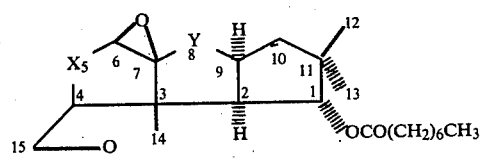

wherein one of X and Y is

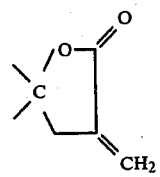

and the other is $>C-OH$, $>C=O$ or

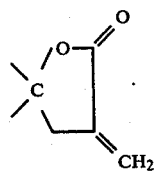

6 Claims, No Drawings

CORIOLIN DERIVATIVES

This invention relates to anti-tumor low-toxicity coriolin derivatives and a process for producing such derivatives.

Coriolin, coriolin B and coriolin C are natural terpenoids which have been extracted and isolated from a culture solution of Coriolus consors, a basidiomycete, by Umezawa et al. [J. Antibiotics 24, 631 (1971), 22, 215 (1969), Tetrahedron Letters 1971, 1955]. As the known coriolin type compounds having an anti-tumor activity, 5-dehydrocoriolin B, 5,8-dehydrocoriolin B (diketocoriolin B) and other derivatives are known in addition to the above-mentioned coriolin and coriolin C (see above-mentioned J. Antibiotics and Tetrahedron Letters).

The compounds of this invention has such a modified chemical structure that the hydroxyl group at the $C_5$- and/or $C_8$-position in coriolin B are replaced with α-methylene 5-members lactone structure.

Thus, there are provided according to this invention, the coriolin derivatives represented by the following general formula (I),

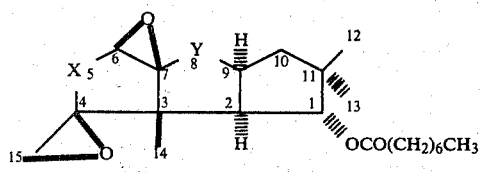

(wherein one of X and Y is

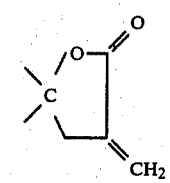

and the other is $>C-OH$, $>C=O$ or

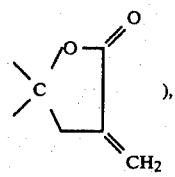

), and a process for producing such derivatives.

The compounds which are subject matter of this invention represented by the above-shown general formula (I) have not only a prominent life-prolonging effect against mouse leukemia L-1210 but also a higher inhibitory activity against the experimental tumor cells such as HeLa cells that the known coriolin compounds, and further the toxicity of the compounds of this invention is relatively low, so that use of these compounds as an anti-tumor preparation is expected.

The principal object of this invention is to provide novel coriolin derivatives having excellent anti-tumor activity and low toxicity and a process for producing such derivatives.

Other objects, features and advantages of this invention, will become apparent from the following detailed description of the invention.

Some typical examples of the compounds of this invention are listed in Table 1 below.

TABLE 1

| No. | X | Y | Name | Appearance m.p. °C. | Molecular formula C.H. Theoretical C.H. Found | Infrared absorption $cm^{-1}$ (KBr tablet) |
|---|---|---|---|---|---|---|
| I | $>C-OH$ | (lactone) | 1α-octanoyl-4β, 15:6β, 7β-dioxide-5β-hydroxy-8(22-methylene-21-butanolide)hirsutane | White needle crystal 165°–167° C. | $C_{27}H_{38}O_7$ C:68.33 H:8.07 C:68.56 H:8.00 | 3500, 2940, 2860, 1765, 1723, 1669, 1468, 1451 1414, 1398, 1371, 1312, 1268, 1227, 1160, 1110 1098, 1050, 1015, 1001, 998, 960, 942, 930 920, 903, 890, 868, 850, 820, 797 782 757, 720, 688 |
| II | $>C=O$ | " | 1α-octanoyl-4β, 15:6β, 7β-dioxide-5-oxo-8(22-methylene-21-butanolide)hirsutane | White needle crystal 165°–166° C. | $C_{27}H_{36}O_7$ C:68.62 H:7.68 C:68.79 H:7.73 | 2940, 2870, 1764, 1730, 1665, 1468, 1417, 1390 1371, 1355, 1300, 1271, 1239, 1168, 1140, 1118 1100, 1061, 1044, 1029, 1005, 985, 935, 905 852, 828, 812, 795, 770, 760, 725, 680 |

TABLE 1-continued

| No. | X | Y | Name | Appearance m.p. °C. | Molecular formula C.H. Theoretical C.H. Found | Infrared absorption cm$^{-1}$ (KBr tablet) |
|---|---|---|---|---|---|---|
| III | (lactone with CH₂) | C—OH | 1α-octanoyl-4β, 15:6β, 7β-dioxide-5(19-methylene-18-butanolide)-8β-hydroxy-hirsutane | White needle crystal 179°–181° C. | $C_{27}H_{38}O_7$ C:68.33 H:8.07 C:67.89 H:7.93 | 3500, 2940, 2870, 1760, 1732, 1662, 1469, 1440 1390, 1370, 1360, 1340, 1325, 1292, 1279, 1222 1190, 1172, 1139, 1110, 1088, 1060, 1017, 985 960, 949, 935, 911, 902, 887, 860, 813 778, 760, 725, 695 |
| IV | " | C=O | 1α-octanoyl-4β, 15:6β, 7β-dioxide-5(19-methylene-18-butanolide)-8-oxo-hirsutane | White needle crystal 186°–187° C. | $C_{27}H_{36}O_7$ C:68.62 H:7.68 C:68.41 H:7.78 | 2950, 1790, 1755, 1665, 1462, 1432, 1420, 1392 1373, 1310, 1281, 1270, 1178, 1160, 1110, 1060 1027, 990, 947, 910, 864, 840, 810, 760 741, 720, 700 |
| V | " | (lactone with CH₂) | 1α-octanoyl-4β, 15:6β, 7β-dioxide-5(19-methylene-18-butanolide)-8(22-methylene-21-butanolide)hirsutane | White needle crystal 243°–244° C. | $C_{31}H_{40}O_8$ C:68.87 H:7.46 C:68.99 H:7.30 | 3400, 2935, 1767, 1723, 1660, 1460, 1370, 1310 1267, 1215, 1160, 1095, 1058, 1017, 1000, 980 952, 931, 914, 878, 860, 810, 760, 740 720, 688 |

The process for producing the compounds of this invention can be expressed by the following reaction formulae:

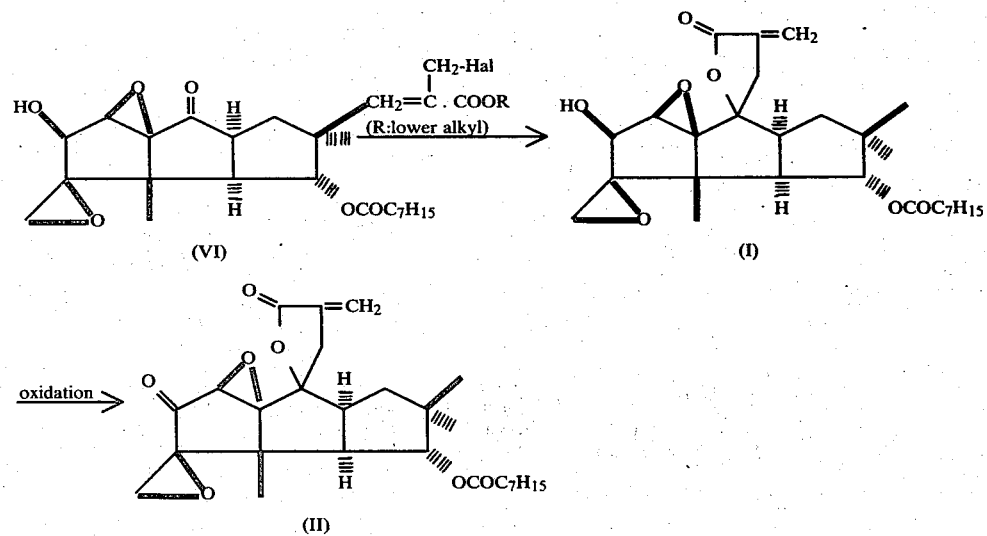

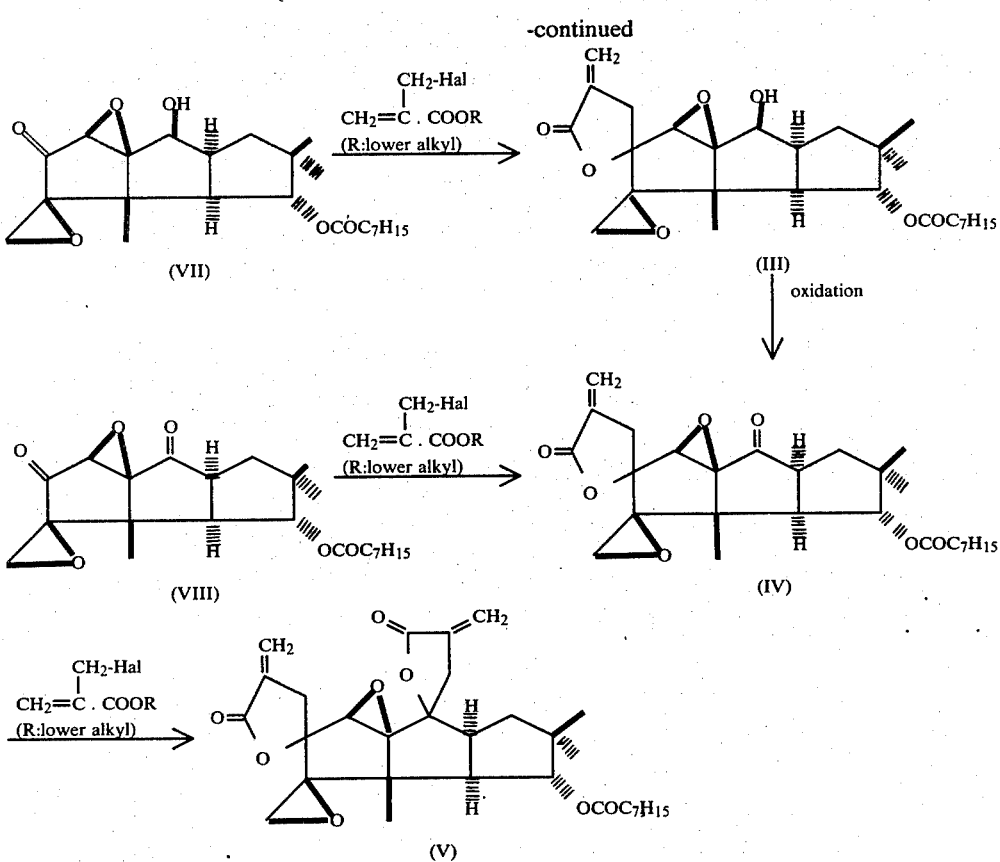

In the above-shown formulae, the compounds (VI), (VII) and (VIII) are the already known compounds which can be obtained by oxidizing coriolin B under various conditions and reported by Umezawa et al. in Tetrahedron Letters No. 22, 1955–1958 (1971), Japanese Patent Laid-Open No. 39698/72 and J. Antibiotics 24(9), 631–635 (1971), respectively. Other compounds can be obtained by using the above-said compounds as starting material. For example, compound (I) can be obtained by reacting 8-dehydrocoriolin B (VI) with an α-halogenomethylacrylic acid ester, particularly its lower alkyl ester, in an anhydrous inert solvent in the presence of metallic zinc. Likewise, compound (III) can be obtained by reacting 5-dehydrocoriolin B (VII) with said reagent.

The reaction of diketocoriolin B (VIII) and said reagent leads to the production of compound (V), but in this case, compound (IV) is also produced as a reaction intermediate and usually a mixture of said both compounds (IV) and (V) is formed, but they can be separated by suitable means such as chromatography. Compound (IV) can be also obtained from oxidization of said compound (III).

The α-halogenomethylacrylic acid esters usable in the above reaction include α-iodomethylacrylic acid methyl ester, α-bromomethylacrylic acid methyl ester, α-bromomethylacrylic acid ethyl ester, α-chloromethylacrylic acid methyl ester, α-chloromethylacrylic acid ethyl ester and the like, but α-bromomethylacrylic acid methyl ester and α-bromomethylacrylic acid ethyl ester are most preferred for the reason of high yield. These esters are also practical as they can be easily synthesized by the method of A. F. Ferris et al. [J. Org. Chem., 20, 780–787 (1955)] according to the following formula:

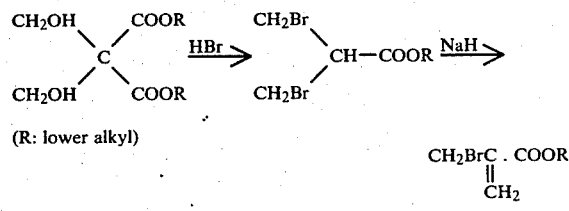

The solvent used in the reaction of this invention may be selected from the ethers such as diethyl ether, diisopropyl ether, tetrahydrofuran, dioxane, etc., hydrocarbons such as benzene, toluene, etc., and mixtures thereof, but tetrahydrofuran and diethyl ether are most preferred.

The α-halogenomethylacrylic acid ester is used in an amount of 1 to 3 equivalents, preferably 1.2 to 2 equivalents, to the coriolin compound used as starting material.

Metallic zinc may be used in powdery, granular, foil-like or capillary form, but it is generally recommended to employ a commercial product which has been activated by a suitable method such as treatment with a dilute hydrochloric acid or a copper salt solution. Such metallic zinc is used in an amount of 1 to 5 equivalents, preferably 1.5 to 3 equivalents, to the coriolin compound used as starting material.

The reaction of this invention is carried out at a temperature of from 20° to 100° C., preferably 50° to 80° C., for the period of 20 minutes to 24 hours, preferably 30 minutes to 5 hours.

Upon completion of the reaction, the reaction mixture is filtered and the filtrate is concentrated or diluted with water and then extracted with a solvent immiscible with water such as ethyl acetate or chloroform, and the extract solution is concentrated, followed by separation and purification of the product by proper means such as recrystallization from an aqueous lower alcohol or a chloroform-ether mixture. However, in case the concentrate is highly impure or in case the resultant product is oily in form, the separation and purification of the product are performed by chromatography using silica gel, alumina or the like as adsorbent and chloroform, ethyl acetate, benzene or a mixture thereof with methanol as eluent, and if necessary, the resultant product is further recrystallized from an aqueous lower alcohol or a chloroform-ether mixture.

The free hydroxyl groups of the thus obtained unsaturated lactones (I) and (III) are then oxidized to obtain the corresponding carbonyl compounds (II) and (IV) by using pyridine, benzene, acetone, acetic acid, dimethyl sulfoxide or a mixture thereof as solvent and chromic acid, manganese dioxide, dicyclohexylcarbodiimide or the like as oxidizing agent.

The best method for oxidizing the hydroxyl group at $C_5$-position of the compound (I) is to use chromic acid in a pyridine solution. In this case, chromic acid as oxidizing agent is used in an amount of 2 to 9 times, preferably 3 to 7 times the molar ratio of the compound (I). The preferred reaction temperature is 1° to 15° C. and reaction time 20 to 80 hours.

Oxidization of the hydroxyl group at $C_8$-position of the compound (III) can in the best method be attained by reacting the compound with 2 to 4 times as much molar quantity of chromic acid as oxidizing agent in a benzene-acetic acid mixed solvent at a temperature of 1° C. to 15° C. for the period of 20 minutes to 3 hours. This method can be also employed for oxidization of the hydroxyl group at $C_5$-position.

For separating the formed compound from the reaction mixture, the latter is filtered and the filtrate is admixed with water and extracted with an organic solvent such as ethyl acetate, chloroform, etc., and the extract solution is concentrated, dried and recrystallized from an aqueous lower alcohol or a chloroform-ether mixture or subjected to silica gel chromatography using chloroform or a chloroform-methanol mixture as solvent.

Now the carcinostatic and antibacterial effects of the compound (I) of this invention are described.

I. Anti-cancer test (1) Effect on HeLa $S_3$ cells

The HeLa $S_3$ cells were scattered in a plastic laboratory dish, 6 cm in diameter, at the rate of $0.7 \times 10^5$ cells/plate by using as a medium an Eagle's MEM (Minimum Essential Medium) [Science, 30, 432–437 (1959)] containing 60 µg/ml of kanamycin and 10% calf serum. On the 2nd day, the medium was removed and a measured quantity of the compound of this invention was added together with a fresh serum-impregnated Eagle's MEM. The cell population at this time was $1.58 \times 10^5$ cells/plate. After adding the compound (I) of this invention thereto, cultures were grown for 3 days and then the medium was removed, followed by washing with physiological saline, treatment with 0.05% trypsin at room temperature for about 15 minutes and pipetting to disperse the cells. The cell number was counted by a counter and percent inhibition (%) was calculated from the number of the control cells (to which no compound was added) to determine $LD_{50}$.

$$\text{Percent inhibiton \%} = \left[ 1 - \frac{\left(\begin{array}{c}\text{cell number after}\\ \text{addition of}\\ \text{compound}\end{array}\right) - \left(\begin{array}{c}\text{cell number at}\\ \text{the time when}\\ \text{compound}\end{array}\right)}{\left(\begin{array}{c}\text{cell number}\\ \text{in control}\end{array}\right) - \left(\begin{array}{c}\text{cell number at}\\ \text{the time when}\\ \text{compound is added}\end{array}\right)} \right] \times 100$$

(2) Effect against L-1210 (lymphatic leukemia strain)

The L-1210 cells ($1 \times 10^5$, 0.05 ml) were inoculated into the $BDF_1$ mouse abdominal cavities ($BDF_1$ means a strain name of mouse), and after lapse of 24 hours, a measured amount of preparation (suspended in 0.5% CMC aqueous solution) was administered once a day for a period of 10 days.

The mice were observed till death, and by comparing the average number of surviving days of the tested mice with that of the control group (to which a 0.5% CMC aqueous solution alone was given), the life prolongation rate was calculated from the following formula:

$$\text{Life prolongation rate} = \frac{\left(\begin{array}{c}\text{average number of}\\ \text{surviving days of}\\ \text{tested group}\end{array}\right) - \left(\begin{array}{c}\text{average number of}\\ \text{surviving days of}\\ \text{control group}\end{array}\right)}{\text{average number of surviving days of control group}} \times 100$$

II. Test results

The inhibitory effect against the HeLa $S_3$ cells and the life-prolonging effect in the cancer (L-1210) affected mice are shown in Table 2 and Table 3, respectively.

TABLE 2

| | Inhibitory effect against HeLa $S_3$ cells | | |
|---|---|---|---|
| Compound No. | Concentration µg/ml | Percent inhibition % | $ID_{50}$ µg/ml |
| I | 4 | 76.2 | 2.1 |
| | 2 | 48.0 | |
| II | 0.2 | 83.2 | 0.12 |
| | 0.1 | 40.2 | |
| III | 2 | 96.6 | 1.1 |
| | 1 | 42.9 | |
| IV | 1 | 71.6 | 0.6 |
| | 0.5 | 43.3 | |
| V | 0.5 | 56.9 | 0.47 |
| | 0.25 | 22.4 | |
| 5-dehydro-coriolin $B_{VI}$ | 1 | 77.6 | 0.76 |
| | 0.5 | 20.0 | |

TABLE 3

| Compound No. | Life-prolonging effect in cancer (L-1210) affected mice Dose μg/mouse × 10 | | | | | |
|---|---|---|---|---|---|---|
| | 200 | 100 | 50 | 25 | 12.5 | 6 |
| I | 130 | 111 | 96 | — | — | — |
| II | Died from toxic effect | 155 | 141 | 141 | 134 | 134 |
| III | 148 | 148 | 141 | 127 | 106 | 99 |
| IV | 127 | 127 | 106 | 113 | 99 | — |
| V | 120 | 99 | — | — | — | — |
| 5-dehydro-coriolin B | Died from toxic effect | Died from toxic effect | 144 | 137 | 138 | 106 |
| VI | | | | | | |

As seen from the above tables, the compounds of this invention are effective for inhibiting growth of the HeLa S$_3$ cells. Particularly, the compound (II) is extremely low in toxicity (ID$_{50}$: 0.12 μg/ml) and works marvelously in preventing growth of the cancerous cells.

Also, the compounds of this invention produce a notable effect in prolonging the life span of the mice which were inoculated with the leukemic germs L-1210, and further, they show no toxicity at the dose of less than 100 μg unlike the compound (VI).

The foregoing facts teach the high availability of the compounds of this invention for the production of antitumor preparations. It will be also noted that compounds I and III can be used as starting material for the preparation of compounds II and IV, respectively.

The process of this invention is further described concretely by way of the following examples.

EXAMPLE 1

1α-octanoyl-4β,15:6β,7β-dioxide-5β-hydroxy-8(22-methylene-21-butanolide)hirsutane 472 mg of 8-dehydrocoriolin B was dissolved in 10 ml of anhydrous tetrahydrofuran, and to this solution, were added 240 mg of zinc powder and 551 mg of α-bromomethylacrylic acid ethyl ester and the mixture was refluxed by heating for 4 hours. The reaction mixture was filtered and the resultant precipitate was washed with ether. The filtrate and the washings were combined. The resultant solution was then washed with water and the resultant organic solvent layer was separated, concentrated under reduced pressure, cooled and allowed to stand overnight.

The precipitated crystals were filtered out, dried and recrystallized with a 6:4 methanol-water mixed solution to obtain 122 mg of the needle-like crystals. Melting point: 165°–167° C.; yield: 22.14%; NMR(CDCl$_3$)δ: 5.53, 6.06 (=CH$_2$).

EXAMPLE 2

1α-octanoyl-4β,15:6β,7β-dioxide-5-oxo-8(22-methylene-21-butanolide)hirsutane 269 mg of 1α-octanoyl-4β,15:6β,7β-dioxide-5β-hydroxy-8(22-methylene-21-butanolide)hirsutane obtained in Example 1 was dissolved in 8 ml of pyridine, and to this solution was added dropwise under agitation and with ice cooling a suspension prepared by adding 290 mg of chromic acid dissolved in 8 ml of pyridine, and the mixture was further reacted at 3°–5° C. for 20 hours.

To the reaction mixture, was further added ethyl acetate, and the formed insolubles were filtered off. The filtrate was washed with water and then concentrated under reduced pressure and dried to obtain 287 mg of reaction product.

This product was dissolved in a small quantity of chloroform, then added to a column packed with 30 ml of silica gel to adsorb said product therein and then eluted with a 0.5% methanol-chloroform mixed solution. The fraction containing the object substance was concentrated, dried and recrystallized with a 6:4 methanol-water mixture to obtain 143 mg of the needle-like crystals. Melting point: 165°–166° C.; yield: 53.4%; NMR(CDCl$_3$)δ: 5.57, 6.10 (=CH$_2$).

EXAMPLE 3

Synthesis of 1α-octanoyl-4β,15:6β,7β-dioxide-5(19-methylene-18-butanolide)-8β-hydroxy-hirsutane 105 mg of 5-dehydrocoriolin B was dissolved in 4 ml of anhydrous tetrahydrofuran and then to this mixture, were added 2 ml of an anhydrous tetrahydrofuran solution containing 30 mg of zinc powder and 73 mg of α-bromomethylacrylic acid ethyl ester, followed by reflux by heating for 1.5 hours. The insolubles were filtered out from the reaction mixture and the formed precipitate was washed with ether. The filtrate was combined with washings and further washed with water, concentrated under reduced pressure, cooled and allowed to stand overnight.

The isolated crystals were filtered off, dried and recrystallized with a 6:4 methanol-water mixture to obtain 40 mg of the object product in the form of needle crystals. Melting point: 179°–181° C.; yield: 32.6%; NMR(CDCl$_3$)δ: 5.67, 6.17 (=CH$_2$).

EXAMPLE 4

Synthesis of 1α-octanoyl-4β,15:6β,7β-dioxide-5(19-methylene-18-butanolide)-8-oxo-hirsutane 100 mg of 1α-octanoyl-4β,7β-dioxide-5(19-methylene-18-butanolide)-8β-hydroxy-hirsutane was dissolved in a mixed solution of 9.6 ml of benzene and 3.2 ml of acetic acid, and to this solution was added a solution of 600 mg of chromic acid dissolved in 1.8 ml of acetic acid under agitation and with ice cooling, followed by further 30-minute reaction at room temperature.

The reaction mixture was filtered and the filtrate was washed repeatedly with water, and thereafter, the benzene layer was separated, concentrated under reduced pressure and allowed to stand overnight.

The separated crude crystals were filtered off, dried and recrystallized with a 6:4 ethanol-water mixture to obtain 80 mg of the object product in the form of needle-like crystals. Melting point: 186°–187° C.; yield: 80.3%; NMR(CDCl$_3$)δ: 5.78, 6.39 (=CH$_2$).

EXAMPLE 5

1α-octanoyl-4β,15:6β,7β-dioxide-5(19-methylene-18-butanolide)-8(22-methylene-21-butanolide)hirsutane 474 mg of diketocoriolin B was dissolved in 6 ml of anhydrous tetrahydrofuran, and to this solution, was added 3 ml of anhydrous tetrahydrofuran solution containing 280 mg of powdered zinc and 704 mg of α-bromomethylacrylic acid methyl ester, followed by refluxing by heating for 30 minutes. After the reaction, the insolubles were filtered out and the filtrate was concentrated, and the resultant crude crystals were recrystallized with a 1:3 chloroform-ether mixture to obtain 161 mg of the object product as needle-like crystals. Melting point: 243°–244° C.; yield: 25.4%; NMR(CDCl$_3$)δ: 5.66, 5.76, 6.17, 6.21 (=C$\underline{H}_2$).

What is claimed is:

1. A coriolin derivative represented by the general formula:

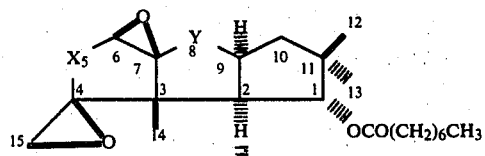

wherein one of X and Y is

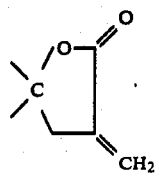

and the other is $>$C—OH, $>$C=O or

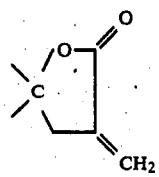

2. 1α-octanoyl-4β,15:6β,7β-dioxide-5β-hydroxy-8(22-methylene-21-butanolide)hirsutane.

3. 1α-octanoyl-4β,15:6β,7β-dioxide-5-oxo-8(22-methylene-21-butanolide)hirsutane.

4. 1α-octanoyl-4β,15:6β,7β-dioxide-5(19-methylene-18-butanolide)-8β-hydroxy-hirsutane.

5. 1α-octanoyl-4β,15:6β,7β-dioxide-5(19-methylene-18-butanolide)-8-oxo-hirsutane.

6. 1α-octanoyl-4β,15:6β,7β-dioxide-5(19-methylene-18-butanolide)-8(22-methylene-21-butanolide)hirsutane.

* * * * *